United States Patent
Mandell

(10) Patent No.: US 10,231,888 B2
(45) Date of Patent: Mar. 19, 2019

(54) WASHABLE REUSABLE CATAMENIAL NAPKIN PAD

(71) Applicant: Eleanor Leah May Mandell, Greenfield, MA (US)

(72) Inventor: Eleanor Leah May Mandell, Greenfield, MA (US)

( * ) Notice: Subject to any disclaimer, the term of this patent is extended or adjusted under 35 U.S.C. 154(b) by 314 days.

(21) Appl. No.: 15/224,686

(22) Filed: Aug. 1, 2016

(65) Prior Publication Data

US 2018/0028370 A1    Feb. 1, 2018

(51) Int. Cl.
*A61F 13/505* (2006.01)
*A61F 13/472* (2006.01)
*A61F 13/15* (2006.01)

(52) U.S. Cl.
CPC .......... *A61F 13/505* (2013.01); *A61F 13/472* (2013.01); *A61F 2013/15276* (2013.01)

(58) Field of Classification Search
CPC .............. A61F 13/505; A61F 13/15691; A61F 2013/15268; A61F 2013/15284
See application file for complete search history.

(56) References Cited

U.S. PATENT DOCUMENTS

| | | | |
|---|---|---|---|
| 1,734,464 A * | 11/1929 | Guinzburg | A61F 13/505 604/397 |
| 2,026,158 A * | 12/1935 | Bennett | A61F 13/505 604/398 |
| 2,700,974 A * | 2/1955 | Roberts | A61F 13/472 604/397 |
| 3,635,221 A * | 1/1972 | Champaigne, Jr. | A61F 13/505 604/364 |
| 3,970,087 A | 7/1976 | Castaneda | |
| 4,678,465 A * | 7/1987 | Avejic | A61F 13/505 604/393 |
| 5,356,402 A | 10/1994 | Gillies | |
| 5,429,627 A | 7/1995 | Johnson | |
| 5,688,258 A * | 11/1997 | Rawat | A61F 13/15203 604/358 |
| 6,764,477 B1 | 7/2004 | Chen | |
| 7,090,666 B2 | 8/2006 | Miskie | |
| 9,024,108 B2 | 5/2015 | McManus | |
| 9,301,886 B2 * | 4/2016 | Fernandez | A61F 13/15268 |
| 2004/0236298 A1 | 11/2004 | Coates | |
| 2014/0114273 A1 | 4/2014 | Sierra | |
| 2016/0030255 A1 | 2/2016 | Rescorl | |

FOREIGN PATENT DOCUMENTS

| | | | |
|---|---|---|---|
| GB | 292464 A | 8/1929 | |
| GB | 1094143 A * | 12/1967 | ............. A61F 13/64 |
| JP | 2011104328 A | 6/2011 | |

* cited by examiner

*Primary Examiner* — Christopher R Harmon

(57) ABSTRACT

A reusable washable catamenial napkin pad is formed from a lightweight oblong fabric sheath or casing which encloses an absorbent cushion and a fluid impermeable liner. The casing is made of a rectangle of cloth which has its long edges folded towards each other and attached only partially in the middle. Then the cushion and liner are slid inside the casing by the user, with the liner on the bottom, forming the pad. The pad is attached by safety pins or similar attachment device to an elastic belt. When the pad has been used and removed from the elastic belt, the three components, namely casing, cushion, and liner, are separated for washing.

3 Claims, 3 Drawing Sheets

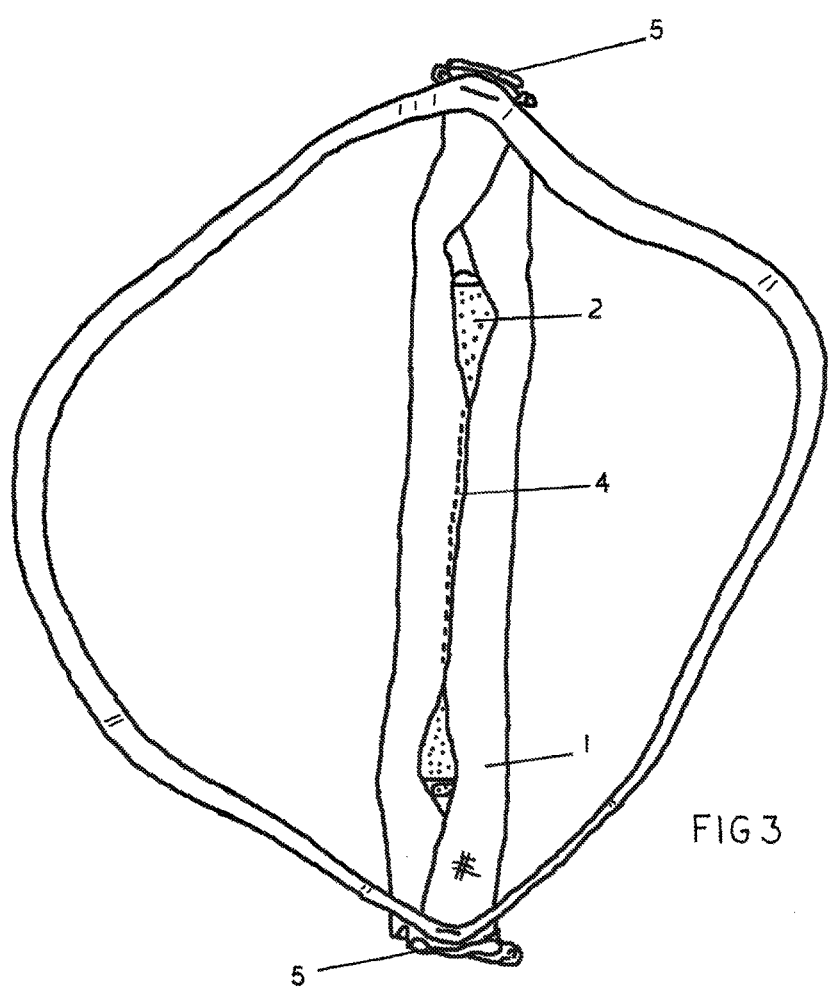

WASHABLE REUSABLE CATAMENIAL NAPKIN PAD

CROSS-REFERENCE TO RELATED APPLICATIONS

Not Applicable

Figure 1:
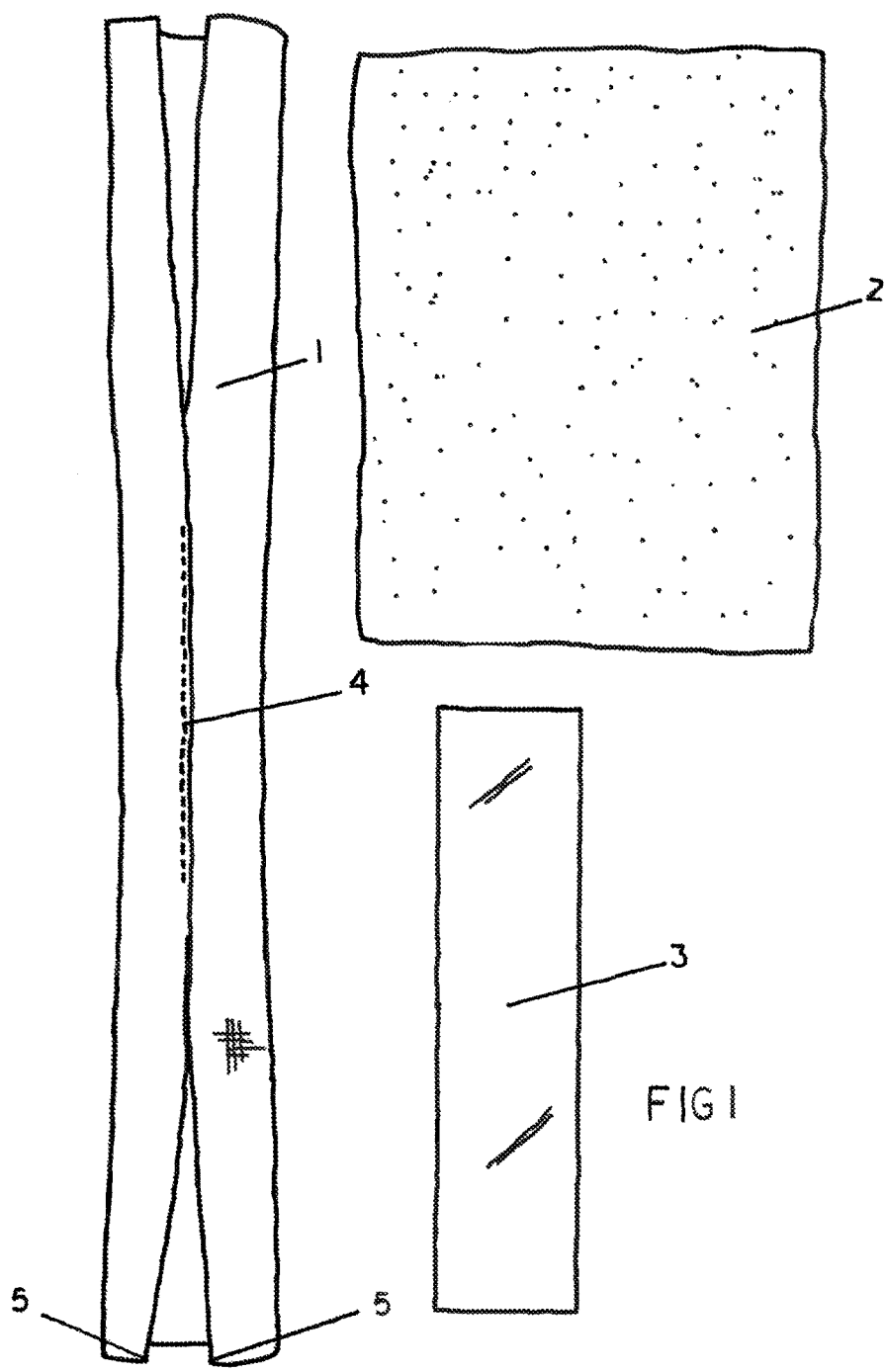

The following is a tabulation of some prior art that presently appears relevant.

U.S. Patents

| Pat. No. | Kind Code | Issue Date | Patentee |
|---|---|---|---|
| 9,301,886 | B2 | Apr. 5, 2016 | Fernandez, Dolores Rubio |
| 9,024,108 | B2 | May 5, 2015 | McManus, Marcia |
| 7,090,666 | B2 | Aug. 15, 2006 | Miskie, Mark |
| 6,764,477 | B1 | Jul. 20, 2004 | Chen, Fung-jou et al |
| 5,429,627 | A | Jul. 4, 1995 | Johnson, Stacey A. |
| 5,356,402 | A | Oct. 18, 1994 | Gillies, Suzanne et al |
| 4,678,465 | A | Jul. 7, 1987 | Avejic, Katarina |
| 3,970,087 | A | Jul. 20, 1976 | Castaneda, Rosa Maria |
| 3,400,718 | A | Sep. 10, 1968 | Saijo, Toshiko |

U.S. Patent Application Publications

| Publication Nr. | Kind Code | Pub. Date | Applicant |
|---|---|---|---|
| 20160030255 | A1 | Feb. 4, 2016 | Rescorl, Linda L. |
| 20140114273 | A1 | Apr. 24, 2014 | Sierra, Diana Beatriz |
| 20040236298 | A1 | Nov. 25, 2004 | Coates, Fredrica V. |

Foreign Patent Documents

| Foreign Doc. Nr. | Cty. Code | Kind Code | Pub. Dt. | App. or Patentee |
|---|---|---|---|---|
| 2011104328 | JP | A | Jun. 2, 2011 | Kubo, Tomoko |
| 292464 | GB | A | Aug. 1, 1929 | Clapin, Emma Augustine |

BACKGROUND OF THE INVENTION

Disposable catamenial products are not affordable in many regions of the world and most reusable catamenial products have drawbacks. In developing countries, girls and women continue to be ostracized and miss school and work when they are menstruating. There is a need for a simple, effective, inexpensive, reusable, and environmentally friendly catamenial product, which is easy to make. Even in countries whose inhabitants can pay the monetary cost of disposable catamenial products, there is a heavy environmental cost both from manufacturing the disposable products and their packaging, and from disposing of them after use. In addition to the monetary and environmental costs of disposable products, tampons specifically may pose health risks as chemical processing residues could be absorbed into the user's body through the internal vaginal membranes, which are known to be highly absorptive. Tampons may also exacerbate menstrual discomfort by virtue of being worn internally next to sensitive organs. For these and other reasons, reusable sanitary products are making a small comeback in developed countries, and social media sites are active in their advice and encouragement for those wanting to switch to reusable products.

Prior Art

Many existing reusable catamenial pads are constructed from layers which are attached, which makes the pads bulky and more difficult to thoroughly clean after use. Current designs are complex to construct, which makes them expensive to produce and discourages those people inclined to sew the pads themselves. Many are designed to attach to a specific form of undergarment, namely a panty with a crotch section of standard dimensions. What is needed is a simple yet secure and effective design that can be made from available fabrics and lining materials, that is easy to sew, easy to wash thoroughly, and doesn't require a specific form of undergarment.

U.S. Pat. No. 3,400,718, Sep. 10, 1968, Toshiko Saijo, teaches a sheath-like sanitary belt that encloses an absorbent layer, with an attached fluid impermeable layer. This sanitary belt would not be easily adapted for users of different sizes and shapes and would be somewhat complex to sew. The belt is not intended to be changed and washed as often as the absorbent layer, and yet it comes into direct contact with body fluids. An improvement to the U.S. Pat. No. 3,400,718 design would be a sheath that was simpler in construction and intended for frequent washing, along with "one size fits most" flexibility.

SUMMARY

A washable reusable catamenial pouch or sanitary napkin pad is formed from three pieces which are not attached, namely a casing, a cushion, and a liner. The casing is constructed from a single substantially rectangular or oblong piece of lightweight fabric such as muslin, with all edges hemmed or overlock stitched to prevent unraveling. The long ends of this oblong piece of lightweight fabric are folded towards each other and joined only for the middle section. This join forms the top of the casing. As used herein the term "top" means the direction facing the body of the user while the term "bottom" means the direction facing away from the body of the user. In this way an open ended, only partially closed sheath is constructed. The cushion is an absorptive cloth. Multiple cushions or cushion layers can be stacked to accommodate heavier menstrual flow or urinary incontinence. The liner is a strip of fluid impermeable material such as plastic or vinyl sheeting, or polyurethane laminate. To form the pad, the cushion is folded and placed on top of the liner and then both are slid to the middle of the casing with the liner on the bottom. Each of the short ends of the casing is overlapped and attached to an elastic belt with safety pins or similar attachment device. The elastic belt goes around the waist of the user and holds the pad securely against the user's body with the cushion at the vaginal opening to collect menstrual fluids. After use the pad is unpinned from the belt and its three component pieces are separated for washing.

Advantages

The current catamenial napkin pad comprises a sheath or casing made of a substantially rectangular piece of cloth, into which is inserted an absorptive cushion and an optional fluid impermeable liner. The sheath or casing is only partially closed, at about the middle of its length, which facilitates removal of the cushion and liner, for washing. The casing attaches to a strip of elastic worn as a belt. This design is inexpensive to produce. The front and the back are identical, which enhances simplicity. The design could also be used as a female urinary incontinence pad or a "mommy-pad" to absorb bodily fluids after childbirth. The design doesn't require much sewing skill and could be produced by hand sewing, a regular sewing machine, or an overlock serger sewing machine. The three components of the pad, namely the casing, the cushion, and the optional liner, could be sourced from either new or repurposed materials.

Compared to the sanitary belt of U.S. Pat. No. 3,400,718, where the casing is designed as part of the belt apparatus, the casing of the present design is part of the pad apparatus. The casing is simple and is intended to be laundered as frequently as the cushion, which is an hygienic improvement over U.S. Pat. No. 3,400,718. The current design is easily adapted for different body shapes and sizes as well as levels of menstrual flow. It requires a minimum of construction steps while still providing highly effective utility.

These and other benefits of one or more aspects will become apparent from a consideration of the ensuing description and accompanying drawings.

DRAWINGS—FIGURES

Figure 2:
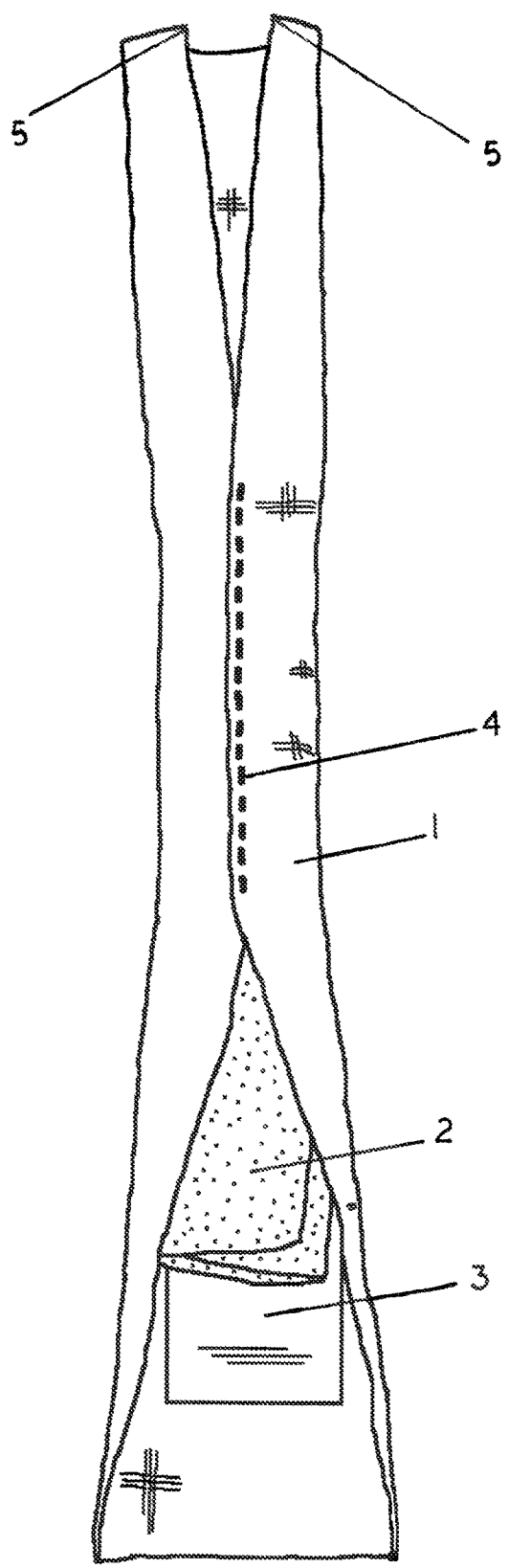

FIG. 1 shows the three separate components of the device
FIG. 2 shows the device being assembled
FIG. 3 shows the device attached to an elastic belt and ready for use.

DRAWINGS—REFERENCE NUMERALS 1 casing
2 cushion
3 liner
4 casing join
5 freely overlapping ends

DETAILED DESCRIPTION

FIG. 1 illustrates the three component pieces of the pad, before they are assembled by the user. The casing 1 is constructed of a substantially rectangular piece of lightweight cloth fabric whose long edges are connected to form the casing join 4, and the freely overlapping ends 5. The casing 1 is open at both ends and only partially joined in the middle to facilitate placement of the cushion 2 and liner 3, while still securing them sufficiently. The cushion 2 is made of soft absorbent material that is compressible, conformable, and non-irritating to the user's skin. The liner 3 is made of a sheet or strip of fluid impermeable substance such as plastic or vinyl sheeting, or polyurethane laminate.

FIG. 2 illustrates the cushion 2 and the liner 3 being positioned inside the casing 1, with the cushion on top towards the user's body and the liner on the bottom away from the user's body. They are slid into the casing and held securely in place by the casing join 4. Assembly of these components prior to use is straightforward.

FIG. 3 illustrates the pad ready for use, with the freely overlapping ends 5 separately stacked and attached with safety pins to an elastic belt, which automatically creates tensioning that provides additional security against cushion 2 and liner 3 displacement. The casing 1 serves multiple functions. It passes fluid down into the cushion 2, it holds the cushion 2 and liner 3 together and in the proper position, it provides structural support, and it attaches the cushion 2 and liner 3 to the elastic belt. The casing also provides a comfortable interface between the liner and the user and helps to prevent any irritation caused by contact between the rough edges of the liner, and the user. The fit is customizable as the casing can be attached to the belt either closer to the casing join, or further away. Also, the belt can be of greater or lesser circumference for different sized users, and can be worn higher or lower on the user's waist to provide the optimal balance of comfort and security.

Conclusion, Ramifications, and Scope

There is a need for an inexpensive, effective, and environmentally friendly catamenial device that is easy to wash thoroughly and easy to sew. This catamenial pad, by its simplicity, lends itself to modification of the relative proportions of the components to achieve optimal utility and comfort for any particular user, depending on their body type, size, and menstrual flow pattern. For example the casing can be made wider to provide greater coverage against fluid leakage and greater stability against the user's body. Or it can be made narrower for less bulk and a more streamlined appearance and feel. The casing can be made longer for larger people or if the user wants the safety pin attachment to land higher on their body. It can also be modified to accommodate a heavier flow of liquid such as from urinary incontinence, by making the casing more capacious and adding layers of cushion. The fluid impermeable liner is optional. Ideally the casing and cushion are made of sustainable eco-friendly long wearing fabrics such as hemp, linen, and bamboo so they will last many years with minimal environmental impact. But poor people can also construct the pad design of repurposed cloth, to achieve the same utility. The description above contains many specificities but these should not be construed as limiting the scope of the embodiments. Instead the scope of the embodiments should be determined by the appended claims and their legal equivalents

What is claimed is:

1. A washable reusable catamenial pad comprising: a folded cloth casing with two opposing longitudinal sides folded together and permanently joined along a length of a middle portion of each side defining a casing join leaving unattached side portions and an open end configuration; a cushion insert positioned within said casing adjacent said casing join wherein said cushion insert comprises a liner and an absorbent material either in a single layer or folded configuration; said liner comprising a single layer fluid impermeable sheeting material.

2. The catamenial pad of claim 1 wherein said casing join is a stitched closure.

3. The catamenial pad of claim 1 wherein said casing join is a non-stitched closure.

* * * * *